United States Patent
Saura Calixto

(10) Patent No.: US 10,272,128 B2
(45) Date of Patent: Apr. 30, 2019

(54) ANTIOXIDANT INGREDIENT WITH LOW CALORIE CONTENT, PROCESS FOR OBTAINING SAME AND USE THEREOF

(71) Applicant: CONSEJO SUPERIOR DE INVESTIGACIONES CIENTÍFICAS (CSIC), Madrid (ES)

(72) Inventor: Fulgencio Diego Saura Calixto, Madrid (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 0 days.

(21) Appl. No.: 14/366,453

(22) PCT Filed: Dec. 20, 2012

(86) PCT No.: PCT/ES2012/070885
§ 371 (c)(1),
(2) Date: Jun. 18, 2014

(87) PCT Pub. No.: WO2013/093161
PCT Pub. Date: Jun. 27, 2013

(65) Prior Publication Data
US 2014/0348925 A1    Nov. 27, 2014

(30) Foreign Application Priority Data
Dec. 20, 2011 (ES) .................................. 201132052

(51) Int. Cl.
| | | |
|---|---|---|
| *A61K 36/87* | (2006.01) | |
| *A23L 33/00* | (2016.01) | |
| *A23L 19/00* | (2016.01) | |
| *A23L 2/02* | (2006.01) | |
| *A23L 2/52* | (2006.01) | |
| *A23L 2/66* | (2006.01) | |
| *A61K 36/185* | (2006.01) | |
| *A21D 2/36* | (2006.01) | |
| *A23L 33/105* | (2016.01) | |
| *A23L 33/20* | (2016.01) | |
| *A23L 33/21* | (2016.01) | |

(52) U.S. Cl.
CPC ............... *A61K 36/87* (2013.01); *A21D 2/36* (2013.01); *A23L 2/02* (2013.01); *A23L 2/52* (2013.01); *A23L 2/66* (2013.01); *A23L 19/09* (2016.08); *A23L 33/00* (2016.08); *A23L 33/105* (2016.08); *A23L 33/20* (2016.08); *A23L 33/21* (2016.08); *A61K 36/185* (2013.01); *A61K 2236/00* (2013.01)

(58) Field of Classification Search
None
See application file for complete search history.

(56) References Cited

U.S. PATENT DOCUMENTS

| 7,629,010 | B2 * | 12/2009 | Passarelli et al. ............ 426/425 |
| 2008/0260935 | A1 | 10/2008 | Alkayali |
| 2009/0214712 | A1 * | 8/2009 | Kang et al. ..................... 426/73 |
| 2011/0195171 | A1 * | 8/2011 | Tieman ......................... 426/595 |

FOREIGN PATENT DOCUMENTS

| EP | 2033526 A1 | 3/2009 |
| ES | 2074031 A1 | 8/1995 |
| ES | 2130092 A1 | 6/1999 |
| ES | 2168223 A1 | 6/2002 |
| ES | 2195007 T3 | 12/2003 |
| ES | 2217979 A1 | 11/2004 |
| ES | 2229575 T3 | 4/2005 |
| ES | 2299288 A1 | 5/2008 |
| JP | 2000023637 A | 1/2000 |
| JP | 2001097872 A | 4/2001 |
| KR | 2003/0015347 A | 2/2003 |
| WO | WO 2011/073052 A1 | 6/2011 |

OTHER PUBLICATIONS

International Search Report for PCT/ES2012/070885, dated Apr. 2, 2013, 19 pgs.
Arranz et al., "Nonextractable polyphenols, usually ignored, are the major part of dietary polyphenols: A study on the Spanish diet", Mol. Nutr. Food Res. 54, pp. 1646-1658 (2010).
Borchani et al., "Effect of drying methods on physico-chemical and antioxidant properties of date fibre concentrates", Food Chem. vol. 125 (4), pp. 1194-1201 (2011).
Fu Li et al, "Antioxidant capacities and total phenolic contents of 62 fruits", Food Chemistry vol. 129 (2), pp. 345-350 (2011).
Herrera et al., "Aspects of antioxidant foods and supplements in health and disease", Nutrition Reviews vol. 67(Suppl. 1) pp. S140-S144 (2009).
Saura-Calixto "Antioxidant dietary fibre: a new functional ingredient", Ernährung/Nutrition vol. 34, pp. 509-514 (2010).
Sun et al., "Antioxidant and antiproliferative activities of common fruits", J. of Agricultural and Food Chemistry vol. 50 (25), pp. 7449-7454 (2002).

(Continued)

*Primary Examiner* — Jennifer A Berrios
(74) *Attorney, Agent, or Firm* — Squire Patton Boggs (US) LLP

(57) ABSTRACT

The present invention relates to an antioxidant ingredient with low calorie content obtainable by a process that comprises the following steps: (a) selecting as raw material at least one fruit and/or plant material with high antioxidant content, greater than 6 g/100 g dry matter; (b) obtaining juice and pulp by means of grinding, squeezing and/or pressing the raw material; (c) extracting sugars from the pulp obtained in the preceding step in order to produce a pulp with low calorie content; (d) dehydrating the pulp by means of a method selected from air drying, low-temperature drying with application of vacuum and/or freeze-drying; and (e) milling the pulp in order to produce the antioxidant ingredient with low calorie content. Likewise, the invention relates to the process for obtaining said ingredient and to the use thereof for the production of functional foods.

17 Claims, No Drawings

(56) References Cited

OTHER PUBLICATIONS

Williamson et al., "Bioavailablility and bioefficacy of polyphenols in humans. II. Review of 93 intervention studies", Am. J. Clin. Nutr. 81 (suppl.): pp. 243S-55S (2005).

Arranz et al. "Nonextractable polyphenols, usually ignored, are the major part of dietary polyphenols: A study on the Spanish diet," Mol. Nutr. Food Res., 2010, vol. 54, pp. 1646-1658.

Akowuah et al. "Effect of extraction temperature on stability of major polyphenols and antioxidant activity of *Orthosiphon stamineus* leaf," Journal of Herbs, Spices & Medicinial Plants (2010), vol. 16, pp. 160-166.

Goni et al. "Towards an updated methodology for measurement of dietary fiber, including associated polyphenols, in food and beverages," Food Research International 42 (2009), pp. 840-846.

Re et al. "Antioxidant activity applying an improved ABTS radical cation decolorization assay", Free Radical Biology & Medicine (1999), vol. 26, Nos. 9/10, pp. 1231-1237.

Saura-Calixto et al. "In vitro determination of the indigestible fraction in foods: an alternative to dietary fiber analysis," J. Agric. Food Chem. (2000), vol. 48, pp. 3342-3347.

Saura-Calixto et al. "Intake and bioaccessibility of total polyphenols in a whole diet," Food Chemistry 101 (2007), pp. 492-501.

Zurita et al. "Improved procedure to determine non-extractable polymeric proanthocyanidins in plant foods," International Journal of Food Sciences and Nutrition (2012), Early Online: 1-4.

Jimenez-Escrig et al. "Guava Fruit (*Psidium guajava* L.) as a New Source of antioxidant dietary fiber," J. Agric. Food Chem (2001), vol. 49, pp. 5489-5493.

Perez-Jimenez et al. "Proanthocyanidin content in foods is largely underestimated in the literature data: An approach to quantification of the missing proanthocyanidins," Food Research International 42 (2009), pp. 1381-1388.

Rufino et al. "Acerola and cashew apple as sources of antioxidants and dietary fibre", Int. Journal of Food Science & Technology (2010), vol. 45, pp. 2227-2233.

Tabernero et al. "The antioxidant capacity of cocoa products: contribution to the Spanish diet," Int. Journal of Food Science & Technology (2006), vol. 41, pp. 28-32.

Jiang J et al. "Short communication: effects of pectolytic enzyme treatmetns on anthocyanins in raspberry juice", 1990 International Journal of Food Science and Technology 25:596-600.

Sun T et al. "Enzyme-catalyzed change of antioxidants content and antioxidant activity of asparagus juice", 2007 Journal of Agricultural and Food Chemistry 55:56-60.

\* cited by examiner

ANTIOXIDANT INGREDIENT WITH LOW CALORIE CONTENT, PROCESS FOR OBTAINING SAME AND USE THEREOF

PRIORITY CLAIM

This application is the National Stage of International Application No. PCT/ES2012/070885, filed Dec. 20, 2012, which claims the benefit of ES Appliction No. P 201132052, filed Dec. 20, 2011, each of which is incorporated by reference in its entirety.

FIELD OF THE ART

The present invention pertains to the field of the food industry. More specifically, it relates to a new functional beverage enriched with an antioxidant vegetable ingredient with low calorie content.

STATE OF THE PRIOR ART

Antioxidants are constituents essential to the diet for the protection of the organism against oxidative damage (cells, DNA, proteins, lipids . . . ) and for its impact on the gene expression. An adequate intake of food and beverages rich in antioxidants causes an increase in the concentration of antioxidants (vitamins C and E, polyphenols, carotenoids) in plasma, which is associated with a significant decrease in risk factors for chronic diseases (cardiovascular, cancer, neurodegenerative) and a decrease in mortality rates (Herrera et al., "Aspects of antioxidant foods and supplements in health and disease" *Nutr. Rev.*, 2009, vol. 67, pp. 140-144).

Properties, metabolism and effects of antioxidants in diet depend on where they exert their action. One part of the antioxidants (type I) consisting of vitamins, polyphenols and carotenoids, are solubilized in the small intestine, where they become bioavailable and can pass, after being absorbed through the intestinal walls, into the blood and be distributed to exert their protective effect in cells and tissues.

Another part of antioxidants in the diet (type II), made up of polyphenols and carotenoids, cross the small intestine unchanged without being bioavailable since they are not solubilized in the digestive fluids. This occurs because they are linked with polymers (proteins, polysaccharides) and fiber of the plant food matrix. However, when this vegetable matrix reaches the large intestine, the action of bacteria in the intestinal microflora, mainly in the colon, causes that antioxidants are released, giving rise to a high antioxidant status that can prevent inflammation and appearance of polyps and crypts, associated with an improvement of intestinal health and prevention of degenerative cellular processes. In addition, various antioxidant metabolites that are absorbed in the colon and pass into the blood, from which are distributed to exert their systemic effects, are released (Williamson G. and Manach, "Bioavailability and bioefficacy of polyphenols in humans. II, Review of 93 intervention studies" *Am. J. Clin. Nutr.*, 2005, vol. 81, pp. 243-255).

Type I antioxidants can be extracted from the food or plant material with solvents, and the different commercial antioxidant concentrates, which are used to enrich foods and functional drinks, are thus obtained. However, the type II antioxidants can not be extracted with solvents and there are no preparations or concentrates thereof in the market. However, it must be noted that a healthy diet, as it is the Mediterranean diet model, contains a significant amount of type II antioxidants, very similar to that of the type I. This suggests that a healthy diet should contain significant amounts of type I and type II antioxidants, or in other words, since in the diet of developed countries the antioxidant intake is low, it seems advisable to increase it in a balanced way (Arranz et al., "Nonextractable polyphenols, usually ignored, are the major part of dietary polyphenols; a study of the Spanish diet", *Mol. Nutr. Food Res.*, 2010, vol. 54, pp. 1646-1658).

The fruit juices and soft drinks are products of high and regular consumption (higher than 250 ml daily per capita in Spain) and are a good vehicle to include those constituents which have significant effects on health and which are usually deficient in common diets in the developed countries.

The beverage industry is very competitive and in recent years is presenting different products with special functional properties to meet the growing demand for healthy products. These include drinks with low calorie content, enriched with antioxidants, fiber, or other substances of recognized properties related to nutrition and health.

In this context, recently beverages which are characterized by their high content of antioxidants and are intended to improve the quality of the diet and thereby contribute to prevent the risk of chronic diseases associated with oxidative stress have appeared on the market. Among these are, for example, juices of pomegranate, acerola, and various tropical fruits, cocoa drinks or alcohol-free wines. There are also dairy products that contain fruit juices. In general, fruits used for the production of this type of beverages have a high content of natural antioxidants, which, when processed, pass to the liquid phase (juice or beverage).

Patent ES 2229575 presents a beverage against oxidative stress produced from extracts and vegetable infusions that contains various non-antioxidant vitamins and preferably 20 to 200 mg/100 kcal of colorless polyphenolic antioxidants. However, the total amount of antioxidants of this invention is less than that of numerous natural beverages (acerola, pomegranate, alcohol-free red wine and others).

Patent ES 2074031 presents an energy drink by mixing fruit juice (orange) and extract of ginseng containing potentially invigorating substances (saponins).

Patent ES 2195007 describes a beverage as a nutritional supplement consisting of water, whey protein, carbohydrates, vitamins and minerals, as well as the procedure of preparation.

Patent ES 2217979 claims a dietary drink consisting of a mixture of lemon juice and grapefruit juice.

Patent ES 2299288 presents a functional beverage based on a non-antioxidant, non-fermented milk product (skim milk) that is mixed with fruit juices—to confer it any antioxidant capacity obviously lower to that of the juices themselves—and a concentrate of conjugated linoleic acid-rich oil. From the analysis of products and found patents it can be concluded that there is a trend in the sector mainly directed to development of natural antioxidant beverages prepared from fruits with a high content of antioxidants, or mixtures of several fruits. Other line presents functional beverages enriched with various compounds (vitamins, minerals, fiber, essential fatty acids, electrolytes, etc.) or supplemented with antioxidants, but in this case the antioxidants are in quantities lower than in juices or natural antioxidant beverages.

However, all the juices or antioxidant beverages natural or prepared with different formulations lack of antioxidants associated to vegetable matrix (type II). Thus, the present invention is directed to retrieve and add natural antioxidants of raw materials (fruits, vegetable matter) that are lost in the current procedures for preparation of juices and beverages.

To do this, a processing of the raw materials selected for their high or exceptional content of antioxidants is carried out. A dry powder of high antioxidant capacity and low caloric content that can be added to the current beverages on the market to give them a higher antioxidant capacity and different features with respect to the antioxidant beverages on the market is obtained. It can also be used as functional ingredient in other food and as a dietary supplement and, in addition, allows to reduce the generation of waste in the processing of certain antioxidant fruits and plant materials.

Therefore, the technical problem that solves the invention is mainly the recovery of a very high percentage of natural antioxidants that are not solubilized or extracted with solvents, but which have specific nutritional properties, of extraordinary interest in nutrition and health.

EXPLANATION OF THE INVENTION

A first object of the present invention is therefore directed to an antioxidant ingredient with low calorie content (less than 20 kcal/100 g) obtainable by a process that comprises the following steps:

(a) selecting a raw material with high antioxidant content (equal to or greater than 6 g/100 g dry matter), said raw material being selected from among at least one fruit and/or plant material;

(b) obtaining juice and pulp from the raw material selected by means of a conventional process that may include grinding, squeezing and/or pressing. For this end, it can be used any equipment or conventional procedure available on the market;

(c) extracting sugars from the pulp obtained in the preceding step in order to produce a pulp with low calorie content (no higher than 20 kcal/100 g). This step of extracting sugars can be carried out preferably by washing the pulp with an ethanol/water dilution. Preferably, said step is carried out to a temperature below 50° C., under stirring and/or by countercurrent, discarding the washing liquids containing sugars of pulp. The ratio of ethanol/water mixture, as well as the liquid ratio of washing/weight of pulp, time and washing temperature, etc., will be determined according to the content of sugar and antioxidants in the raw material;

(d) complete dehydration of pulp, preferably by means of a method selected from air drying (trays or other systems); low-temperature drying, preferably below 70° C., with application of vacuum and/or o freeze-drying;

(e) after dehydrating the pulp, preferably to a moisture content less than or equal to 6%, the dehydrated pulp is subjected to grinding.

This step of grinding or milling can be carried out with hammer mills, centrifugal mills and/or any micronization or encapsulation system, giving rise to a dry powder with a particle size preferably less than 0.5 mm, which constitutes the functional ingredient rich in antioxidants and fiber and low in calories.

Additionally, it is an object of the invention the process of obtaining the antioxidant ingredient with low calorie content according to the aforementioned steps.

Likewise, it is an object of the invention the use of said antioxidant ingredient with low calorie content for preparing functional beverages, preferably for the preparation of fruit juices, milkshakes, milk drinks and other beverages with antioxidant properties, with low calorie content and high dietary fiber content (generally greater than 6 g fiber/100 g product or 3 g/100 kcal product).

DETAILED DESCRIPTION OF THE INVENTION

As stated above, a first object of the present invention is therefore directed to an antioxidant ingredient with low calorie content (less than 20 kcal/100 g) obtainable by a process that comprises the following steps:

(a) selecting a raw material with high antioxidant content (equal to or greater than 6 g/100 g dry matter), said raw material being selected from among at least one fruit and/or plant material;

(b) obtaining juice and pulp from the raw material selected by means of a conventional process that may include grinding, squeezing and/or pressing.

For this end, it can be used any equipment or conventional procedure available on the market;

(c) extracting sugars from the pulp obtained in the preceding step in order to produce a pulp with low calorie content (no higher than 20 kcal/100 g). This step of extracting sugars can be carried out preferably by washing the pulp with an ethanol/water dilution. Preferably, said step is carried out to a temperature below 25 50° C., under stirring and/or by countercurrent, discarding the washing liquids containing sugars of pulp. The ratio of ethanol/water mixture, as well as the liquid ratio of washing/weight of pulp, time and washing temperature, etc., will be determined according to the content of sugar and antioxidants in the raw material;

(d) complete dehydration of pulp, preferably by means of a method selected from air drying (trays or other systems); low-temperature drying, preferably below 70° C., with application of vacuum and/or o freeze-drying;

(e) after dehydrating the pulp, preferably to a moisture content less than or equal to 6%, the dehydrated pulp is subjected to grinding. This step of grinding or milling can be carried out with hammer mills, centrifugal mills and/or any micronization or encapsulation system, to a dry powder with a particle size preferably less than 0.5 mm, which constitutes the functional ingredient rich in antioxidants and fiber and low in calories.

In a particular embodiment of the invention, the process may comprise a further step of preparing the raw material by means of washing the same. In this way, it is possible to remove leaves, stems, soil particles, traces of pesticides, etc., that may be present in the selected raw material. In order to carry out this washing step, it can be used any of the conventional equipment for washing of vegetables, such as vibrators, air and water flows, conveyor belts to hoppers, as well as any other element suitable for this purpose. Likewise, in a particular embodiment in which the pulp obtained from the raw material includes seeds, pips and/or any fraction or impurity of the pulp, the process may include a step of separating and removing the same prior to the extraction of sugars. This step can be carried out with different machinery existing in the market, such as for example perforated grids, rotary cylinders, centrifuges, etc.

In a particular manner, the selection of the raw material used in the process is carried out according to its antioxidant content. In this way, the raw material (fruit and/or plant material) is selected preferably from one that meets the following conditions:

(a) First, that it originally has a high concentration of antioxidants (such as for example grape, pomegranate, cocoa or tropical fruits like guava, acerola, camu camu and many others). In general, it is understood as a high concentration of oxidants that one which contains at least 6 grams of total antioxidants per 100 grams of dry matter;

(b) and that, likewise, once processed according to the steps described above it gives rise to a dry powder with a composition approximately equal to the following:

| Composition | % by weight |
|---|---|
| Water (moisture) | 2-10% |
| Total antioxidants (vitamins, polyphenols, carotenoids) | 6-35% |
| Type II antioxidants (linked to vegetable matrix) | 5-30% |
| Type I antioxidants (extractable with solvents) | 1-5% |
| Sugars | 0-5% |
| Polysaccharides and lignin | 10-40% |
| Proteins | 2-10% |
| Minerals and other natural constituents (vitamins, organic acids, terpenes, chlorophyll, etc.) | 2-8% |

In a particular embodiment in which the raw material of the process consists of a plant material with low water content (generally lower than 15%), the process would be carried out without including the step (b) and the process would begin with the step of milling (step (e)), followed by extraction of sugars (c) and dehydration (d).

As described above, it is also an object of the invention the process for obtaining the antioxidant ingredient with low calorie content according to the aforementioned steps.

In addition, as mentioned, it is also an object of the invention the use of the antioxidant ingredient with low calorie content for preparing functional beverages, preferably for the preparation of fruit juices, milkshakes, milk drinks and other beverages with antioxidant properties, low calorie content and high dietary fiber content (generally greater than 6 g fiber/100 g product or 3 g/100 kcal of product). Additionally, the antioxidant ingredient object of the invention can be used in the preparation of a wide range of functional foods and products related to food and health, including dietary supplements. These products are characterized by containing a qualitative and quantitatively important amount of antioxidants that they currently lack, resulting in a type of antioxidant beverage with distinctive features and higher nutritional quality.

In particular, the functional beverage can be obtained by the addition of the antioxidant ingredient with low calorie content object of the invention to a fruit juice used as raw material (stage 1) giving rise to a natural type I and II antioxidant-rich juice, without increasing the caloric value of the original juice. Preferably, it will be use the ingredient with a particle size suitable for not affecting, or doing it minimally, to the sensory properties of the juice, for which a method of micronization or encapsulation can be used.

Additionally, the amount of antioxidant ingredient added to the functional beverage will be preferably in the order of 10-15 g per 200 ml, which involves providing the quantities recommended of fiber and antioxidants for a healthy diet.

In other particular embodiments of the invention, the obtained ingredient can also be used for other functional beverages, adding it to juices or mixes of juices of various fruits, which may or may not include the juice obtained in step (b) of the described process; milk and other dairy products, as well as any other type of beverages and soft drinks.

Furthermore, the antioxidant ingredient can also be used as a food ingredient in cereal products (cookies, snacks, breads, breakfast cereals, . . . ) and in any type of functional food or enriched; as a dietary supplement for gastrointestinal health (regulation, prevention of inflammation, prebiotic, prevention of polyps and aberrant crypts) and prevention of risk factors for chronic diseases (oxidative stress, inflammation, hypercholesterolemia, hyperglycemia or hypertension).

Finally, it could also be used as an ingredient of various products directed to the food and health.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art in part from the description and in part from the practice of the invention. The following examples are provided by way of illustration, and they are not intended to be limiting of the present invention. Furthermore, the present invention covers all possible combinations of particular and preferred embodiments described herein.

EXAMPLES

Example 1

Obtaining of the Antioxidant Ingredient 10 kg of white grape, Ariel variety, previously washed, are subjected to pressing (conventional hydraulic press), achieving 6.5 liters of juice or grape most and 1.2 kg of grape pomace or fresh pulp with skins, pips, and small remains of stems.

The obtained grape pomace is subjected to a mixture of ethanol/water (80:20) within a container under stirring, in the following conditions:

Ethanol/water and grape pomace ratio: 1 liter per 100 g of grape pomace;
Temperature: 37° C.;
Time: 10 minutes;

Next, the grape pomace-alcohol-water mixture is subjected to a step of decanting or centrifuging, removing the liquid phase and obtaining the sugar-free grape pomace. Said grape pomace is subsequently subjected to a screening process in order to separate pips and remains of stems. Once lyophilized, the seed-free pulp and stems is subjected to grinding in a centrifugal mill with sieve (particle size <5 mm), obtaining 390 g of dry powder that constitutes the antioxidant ingredient with low calorie content, general composition of which in fundamental constituents is:

Moisture: 4.5%
Type II antioxidants: 18.1%
Type I antioxidants: 2.7%
Total antioxidants: 20.8%
Polysaccharides and lignin: 39.0%
Sugars: (<0.5%)

Example 2

Obtaining of Functional Beverage

Once the antioxidant ingredient is obtained, a functional beverage is prepared from the same by adding 300 ml of juice or grape must obtained in the pressing of grapes, of 15 g ingredient. Following the addition of the ingredient, and subsequent stirring, a colloidal dilution or suspension of the functional beverage is obtained.

REFERENCES CITED IN THE APPLICATION

Herrera et al., "Aspects of antioxidant foods and supplements in health and disease" *Nutr. Rev.*, 2009, vol. 67, pp. 140-144

Williamson G. y Manach, "Bioavailability and bioefficacy of polyphenols in humans. II, Review of 93 intervention studies" *Am. J. Clin. Nutr.*, 2005, vol. 81, pp. 243-255

Arranz et al., "Nonextractable polyphenols, usually ignored, are the major part of dietary polyphenols; a study of the Spanish diet", *Mol. Nutr. Food Res.*, 2010, vol. 54, pp. 1646-1658

The invention claimed is:

1. An antioxidant ingredient with low calorie content obtained by a process that comprises the following steps:
   (a) selecting as raw material at least one fruit and/or plant material with high antioxidant content, equal to or greater than 6 g/100 g dry matter;
   (b) obtaining juice and pulp by means of grinding, squeezing and/or pressing the raw material;
   (c) extracting sugars from the pulp obtained in the preceding step, wherein the extraction of sugars from the pulp is carried out by washing the pulp with an ethanol and water dilution and wherein the extraction of sugars from the pulp is carried out at a temperature ranging from 25-50° C. and by stirring and/or countercurrent in order to produce a pulp with low calorie content;
   (d) dehydrating the pulp by means of a method selected from air drying, low-temperature drying with application of vacuum and/or freeze-drying;
   (e) milling the pulp in order to produce the antioxidant ingredient with low calorie content;
   wherein the antioxidant ingredient with low calorie content contains less than 20 kcal/100 g; the antioxidant ingredient with low calorie content comprises a total of antioxidants approximately equal to 6-35% in percentage by weight and the antioxidant ingredient with low calorie content comprises type II antioxidants approximately equal to 5-30% in percentage by weight.

2. The antioxidant ingredient according to claim 1, wherein the process comprises a further step of preparing the raw material by washing thereof.

3. The antioxidant ingredient according to claim 1, wherein after the step of obtaining the pulp, the process comprises a further step of removing seeds, pips, and/or impurities present in the pulp, prior to the extraction of sugars.

4. The antioxidant ingredient according to claim 1, wherein the step of milling is carried out with hammer mills, centrifugal mills and/or micronization or encapsulation, giving rise to a dry powder with a particle size lower than 0.5 mm.

5. The antioxidant ingredient according to claim 1, wherein the fruit or plant material used as raw material is selected from grape, pomegranate, cocoa, acerola, guava, camu camu and other tropical fruits, as well as any combinations thereof.

6. The antioxidant ingredient according to claim 1, characterized in that it comprises the following composition, in percentage by weight, approximately equal to the following:

| | |
|---|---|
| Water | 2-10%; |
| Type I antioxidants, extractable with solvents | 1-5%; |
| Polysaccharides and lignin | 10-40%; |
| Proteins | 2-10%; |
| Minerals, vitamins and other natural constituents | 2-8%; and |
| Sugars | 0-5%. |

7. The antioxidant ingredient according to claim 1, characterized in that in the step of dehydrating d), the drying is carried out at temperatures below 70° C.

8. The antioxidant ingredient according to claim 1, characterized in that in step d), the dehydration of the pulp is carried out to a moisture content less than or equal to 6%.

9. A process for obtaining an antioxidant ingredient, characterized in that it comprises the following steps:
   (a) selecting as raw material at least one fruit and/or plant material with high antioxidant content, equal to or greater than 6 g/100 g dry matter;
   (b) obtaining juice and pulp by means of grinding, squeezing and/or pressing the raw material;
   (c) extracting sugars from the pulp obtained in the preceding step, where the extraction of sugars from the pulp is carried out by washing the pulp with an ethanol and water dilution and wherein the extraction of sugars from the pulp is carried out at a temperature ranging from 25-50° C. and by stirring and/or countercurrent in order to produce a pulp with low calorie content;
   (d) dehydrating the pulp by means of a method selected from air drying, low-temperature drying with application of vacuum and/or freeze-drying;
   (e) milling the pulp in order to produce the antioxidant ingredient with low calorie content;
   wherein the antioxidant ingredient with low calorie content contains less than 20 kcal/100 g; the antioxidant ingredient with low calorie content comprises a total of antioxidants approximately equal to 6-35% in percentage by weight and the antioxidant ingredient with low calorie content comprises type II antioxidants approximately equal to 5-30% in percentage by weight.

10. A functional food comprising the antioxidant ingredient of claim 1.

11. The functional food of claim 10, wherein said functional food is a functional beverage.

12. The functional beverage of claim 11, wherein said functional beverage is selected from fruit juices, milkshakes, and milk drinks.

13. The antioxidant ingredient according to claim 1, characterized in that in the step of dehydrating d), the drying is carried out at temperatures below 70° C., and additionally the dehydration of the pulp is carried out to a moisture content less than or equal to 6%.

14. The process of claim 9, wherein the step of milling is carried out with hammer mills, centrifugal mills and/or micronization or encapsulation, giving rise to a dry powder with a particle size lower than 0.5 mm.

15. The process of claim 9, wherein the antioxidant ingredient comprises the following composition, in percentage by weight, approximately equal to the following:

| | |
|---|---|
| Water | 2-10%; |
| Type I antioxidants, extractable with solvents | 1-5%; |
| Polysaccharides and lignin | 10-40%; |
| Proteins | 2-10%; |
| Minerals, vitamins and other natural constituents | 2-8%; and |
| Sugars | 0-5%. |

16. The antioxidant ingredient with low calorie content of claim 1, characterized in that in the step (c) the extraction of sugars from the pulp is carried out at a temperature of 37° C.

17. The process of claim 9, wherein the extraction step (c) is carried out at a temperature of 37° C.

* * * * *